(12) United States Patent
Matsuyama et al.

(10) Patent No.: US 11,670,398 B2
(45) Date of Patent: Jun. 6, 2023

(54) METHOD FOR DETERMINING PHARMACOKINETICS OF AXITINIB AND METHOD FOR PREDICTING THERAPEUTIC EFFECT OF AXITINIB BASED ON PHARMACOKINETICS OF AXITINIB

(71) Applicants: Yamaguchi University, Yamaguchi (JP); Toyo Kohan Co., Ltd., Tokyo (JP)

(72) Inventors: Hideyasu Matsuyama, Ube (JP); Yoshihiko Hamamoto, Ube (JP); Yusuke Fujita, Ube (JP); Yoshiaki Yamamoto, Ube (JP); Ryouichi Tsunedomi, Ube (JP); Mitsuyoshi Oba, Kudamatsu (JP); Hirofumi Yamano, Kudamatsu (JP); Yukiha Ishikawa, Kudamatsu (JP)

(73) Assignees: Yamaguchi University, Yamaguchi (JP); Toyo Kohan Co., Ltd., Tokyo (JP)

( * ) Notice: Subject to any disclaimer, the term of this patent is extended or adjusted under 35 U.S.C. 154(b) by 772 days.

(21) Appl. No.: 16/613,507

(22) PCT Filed: May 18, 2018

(86) PCT No.: PCT/JP2018/019281
§ 371 (c)(1),
(2) Date: Nov. 14, 2019

(87) PCT Pub. No.: WO2018/212320
PCT Pub. Date: Nov. 22, 2018

(65) Prior Publication Data
US 2021/0158893 A1 May 27, 2021

(30) Foreign Application Priority Data
May 19, 2017 (JP) .............................. JP2017-100043

(51) Int. Cl.
*G16B 20/20* (2019.01)
*G01N 33/53* (2006.01)
*G16C 20/30* (2019.01)

(52) U.S. Cl.
CPC ............. *G16B 20/20* (2019.02); *G01N 33/53* (2013.01); *G16C 20/30* (2019.02)

(58) Field of Classification Search
CPC ............ C12Q 1/6886; C12Q 2600/106; C12Q 2600/156; G01N 33/53; G16C 20/30; C12M 1/34
(Continued)

(56) References Cited

U.S. PATENT DOCUMENTS

2017/0184602 A1 6/2017 Martini et al.
2019/0322671 A1* 10/2019 Bourque et al. ..... C07D 487/04

FOREIGN PATENT DOCUMENTS

JP 2010-263810 11/2010
JP 2015-210268 11/2015

OTHER PUBLICATIONS

European Search Report based on co-pending European Patent Application No. 18802316.2, dated Jan. 15, 2021, 7 pages.
(Continued)

*Primary Examiner* — Thinh T Nguyen
(74) *Attorney, Agent, or Firm* — McCarter & English, LLP

(57) ABSTRACT

It is intended to conveniently determine the pharmacokinetics of axitinib and to predict the therapeutic effect of axitinib. The present invention provides a method for determining the pharmacokinetics of axitinib, comprising the step of calculating a predicted pharmacokinetic parameter of axitinib using specific gene polymorphisms and background factors regarding a test subject.

13 Claims, 10 Drawing Sheets

(58) Field of Classification Search
USPC .......................................................... 702/19
See application file for complete search history.

(56) References Cited

OTHER PUBLICATIONS

Yamamoto, Yoshiaki, et al., "Pharmacogenetics-based area-under-curve model can predict efficacy and adverse events from axitinib in individual patients with advanced renal cell carcinoma", Oncotarget, Mar. 30, 2018, vol. 9, No. 24, pp. 17160-17170.
Matsuyama, H., et al., "Prediction of total clearance by UGT1A and ABC genes Polymorphisms can predict tumor response and proteinuria in axitinib treatment for advanced renal cell carcinoma", Annals of Oncology, 2016, vol. 27, No. 6, p. 1.
Yamamoto, Yoshiaki, et al., "Pharmacogenetics-based area-under-curve model can predict efficacy and adverse events of axitinib in the treatment of advanced renal cell carcinoma", International Journal of Urology, Oct. 1, 2018, vol. 25, No. 1, p. 1.
Patson, Brian, et al., "Pharmacokinetic Evaluation of Axitinib", 2012, Expert Opinion on Drug Metabolism & Toxicology, vol. 8, No. 2, pp. 259-270.
Rini, Brian I., et al., "Axitinib in Metastatic Renal Cell Carcinoma: Results of a Pharmacokinetic and Pharmacodynamic Analysis", The Journal of Clinical Pharmacology, 2013, vol. 53, No. 5, pp. 491-504.
International Search Report based on co-pending International Application No. PCT/JP2018/019281, dated Aug. 14, 2018—2 Pages.

* cited by examiner

Figure 3-1

| NO | UGT1A | | | | | | |
|----|------|------|------|------|------|------|------|
| | 1*6 | 1*28 | 1*60 | 7*12 | 7*2 | 9*1b | 1*93 |
| | 211G>A | TA6>TA7 | -3279T>G | -57T>G | 387T>G | -118T9>T10 | -3156G>A |
| 1 | G/G | TA6/TA6 | T/T | T/T | T/T | T10/T10 | G/G |
| 2 | G/G | TA6/TA6 | T/T | T/T | T/T | T10/T10 | G/G |
| 3 | G/A | TA6/TA6 | T/T | T/G | T/G | T9/T10 | G/G |
| 4 | G/G | TA6/TA6 | T/T | T/T | T/T | T10/T10 | G/G |
| 5 | G/A | TA6/TA6 | T/T | T/G | T/G | T9/T10 | G/G |
| 6 | G/A | TA6/TA6 | T/T | T/G | T/G | T9/T10 | G/G |
| 7 | G/G | TA6/TA6 | G/G | T/T | G/G | T9/T9 | G/G |
| 8 | G/A | TA6/TA6 | T/T | T/G | T/G | T9/T10 | G/G |
| 9 | G/G | TA6/TA6 | G/G | T/T | G/G | T9/T9 | G/G |
| 10 | G/G | TA6/TA6 | T/G | T/T | T/G | T9/T10 | G/G |
| 11 | G/G | TA6/TA6 | T/T | T/T | T/T | T10/T10 | G/G |
| 12 | G/G | TA6/TA6 | T/T | T/T | T/T | T10/T10 | G/G |
| 13 | G/G | TA6/TA6 | T/G | T/T | T/G | T9/T10 | G/G |
| 14 | G/G | TA6/TA6 | T/T | T/T | T/T | T10/T10 | G/G |
| 15 | G/G | TA6/TA7 | T/G | T/G | T/G | T9/T10 | G/A |
| 16 | G/A | TA6/TA6 | T/T | T/G | T/G | T9/T10 | G/G |
| 17 | G/G | TA6/TA7 | T/G | T/T | T/T | T10/T10 | G/A |
| 18 | G/G | TA6/TA6 | T/G | T/T | T/G | T9/T10 | G/G |
| 19 | G/A | TA6/TA6 | T/T | T/G | T/G | T9/T10 | G/G |
| 20 | G/G | TA6/TA7 | G/G | T/G | G/G | T9/T10 | G/A |
| 21 | G/G | TA6/TA6 | T/G | T/T | T/G | T9/T10 | G/G |
| 22 | G/G | TA6/TA6 | T/T | T/T | T/T | T9/T10 | G/G |
| 23 | G/A | TA6/TA7 | T/G | G/G | G/G | T10/T10 | G/A |
| 24 | G/A | TA6/TA6 | T/T | T/G | T/G | T9/T10 | G/G |
| 25 | G/G | TA6/TA7 | T/G | T/T | T/G | T9/T10 | G/A |
| 26 | G/A | TA6/TA6 | T/T | T/G | T/G | T9/T10 | G/G |
| 27 | G/G | TA6/TA6 | T/T | T/T | T/T | T10/T10 | G/G |
| 28 | G/G | TA6/TA6 | T/G | T/T | T/G | T9/T10 | G/G |
| 29 | G/A | TA6/TA6 | T/T | T/G | T/G | T9/T10 | G/G |
| 30 | G/G | TA6/TA6 | T/G | T/T | T/G | T9/T10 | G/G |
| 31 | G/G | TA6/TA6 | T/T | T/T | T/T | T10/T10 | G/G |
| 32 | G/G | TA6/TA6 | T/G | T/T | T/G | T9/T10 | G/G |
| 33 | G/G | TA6/TA6 | T/T | T/T | T/T | T10/T10 | G/G |
| 34 | G/G | TA6/TA6 | T/T | T/T | T/T | T10/T10 | G/G |
| 35 | G/G | TA6/TA6 | T/T | T/T | T/T | T10/T10 | G/G |
| 36 | G/G | TA6/TA6 | T/T | T/T | T/T | T10/T10 | G/G |
| 37 | G/G | TA7/TA7 | G/G | T/T | T/T | T10/T10 | A/A |
| 38 | G/G | TA6/TA6 | T/T | T/T | T/T | T10/T10 | G/G |
| 39 | G/G | TA6/TA6 | T/T | T/T | T/T | T10/T10 | G/G |
| 40 | G/G | TA6/TA7 | G/G | T/T | G/G | T9/T9 | G/A |
| 41 | G/G | TA6/TA6 | T/T | T/T | T/T | T10/T10 | G/G |
| 42 | G/G | TA6/TA6 | T/T | T/T | T/T | T10/T10 | G/G |
| 43 | G/A | TA6/TA7 | T/G | T/G | G/G | T9/T10 | G/A |
| 44 | G/G | TA6/TA6 | T/T | T/T | T/G | T10/T10 | G/G |

Figure 3-2

|    | rs2740574 | rs4986910 | rs776746 | rs10264272 |
|----|-----------|-----------|----------|------------|
|    | CYP3A     |           |          |            |
|    | 4*1b      | 4*3       | 5*3      | 5*6        |
| NO | 392A>G    | 1334T>C   | 6986A>G  | 14690G>A   |
| 1  | A/A       | T/T       | G/G      | G/G        |
| 2  | A/A       | T/T       | G/G      | G/G        |
| 3  | A/A       | T/T       | G/A      | G/G        |
| 4  | A/A       | T/T       | G/G      | G/G        |
| 5  | A/A       | T/T       | G/G      | G/G        |
| 6  | A/A       | T/T       | G/G      | G/G        |
| 7  | A/A       | T/T       | G/G      | G/G        |
| 8  | A/A       | T/T       | G/A      | G/G        |
| 9  | A/A       | T/T       | G/G      | G/G        |
| 10 | A/A       | T/T       | G/A      | G/G        |
| 11 | A/A       | T/T       | G/A      | G/G        |
| 12 | A/A       | T/T       | G/G      | G/G        |
| 13 | A/A       | T/T       | G/A      | G/G        |
| 14 | A/A       | T/T       | G/A      | G/G        |
| 15 | A/A       | T/T       | G/A      | G/G        |
| 16 | A/A       | T/T       | G/A      | G/G        |
| 17 | A/A       | T/T       | G/G      | G/G        |
| 18 | A/A       | T/T       | G/G      | G/G        |
| 19 | A/A       | T/T       | G/G      | G/G        |
| 20 | A/A       | T/T       | G/G      | G/G        |
| 21 | A/A       | T/T       | G/A      | G/G        |
| 22 | A/A       | T/T       | G/A      | G/G        |
| 23 | A/A       | T/T       | G/A      | G/G        |
| 24 | A/A       | T/T       | G/G      | G/G        |
| 25 | A/A       | T/T       | G/G      | G/G        |
| 26 | A/A       | T/T       | G/A      | G/G        |
| 27 | A/A       | T/T       | G/G      | G/G        |
| 28 | A/A       | T/T       | G/G      | G/G        |
| 29 | A/A       | T/T       | G/G      | G/G        |
| 30 | A/A       | T/T       | G/A      | G/G        |
| 31 | A/A       | T/T       | G/G      | G/G        |
| 32 | A/A       | T/T       | G/G      | G/G        |
| 33 | A/A       | T/T       | G/G      | G/G        |
| 34 | A/A       | T/T       | G/G      | G/G        |
| 35 | A/A       | T/T       | G/G      | G/G        |
| 36 | A/A       | T/T       | G/G      | G/G        |
| 37 | A/A       | T/T       | G/A      | G/G        |
| 38 | A/A       | T/T       | G/A      | G/G        |
| 39 | A/A       | T/T       | G/G      | G/G        |
| 40 | A/A       | T/T       | G/G      | G/G        |
| 41 | A/A       | T/T       | G/A      | G/G        |
| 42 | A/A       | T/T       | G/G      | G/G        |
| 43 | A/A       | T/T       | G/A      | G/G        |
| 44 | A/A       | T/T       | G/G      | G/G        |

Figure 3-3

| | rs2231142 | rs1128503 | rs2032582 | rs1045642 | rs4974539 | rs35305980 |
|---|---|---|---|---|---|---|
| | | ABC | | | | |
| | BCRP | MDR1 | MDR1 | MDR1 | CPN2 | OR2B11 |
| NO | 421C>A | 1236T>C | 2677G>T/A | 3435C>T | Ref:G, Var:A | Ref:GA, Var:G |
| 1 | C/A | T/T | T/G | C/T | Ref/Ref | Ref/Ref |
| 2 | C/A | T/C | T/G | C/T | Ref/Ref | Var/Var |
| 3 | C/A | T/C | T/G | C/T | Hetero | Var/Var |
| 4 | C/C | C/C | A/A | C/C | Var/Var | Hetero |
| 5 | C/C | T/T | T/T | T/T | Hetero | Var/Var |
| 6 | C/A | T/C | G/G | C/C | Hetero | Var/Var |
| 7 | C/C | T/T | T/T | T/T | Ref/Ref | Hetero |
| 8 | C/A | T/T | T/T | T/T | Hetero | Hetero |
| 9 | C/C | T/T | T/T | T/T | Var/Var | Hetero |
| 10 | C/C | T/T | T/T | C/T | Hetero | Ref/Ref |
| 11 | C/C | T/C | T/A | C/T | Hetero | Var/Var |
| 12 | C/A | T/T | T/T | C/T | Var/Var | Hetero |
| 13 | C/C | T/C | T/G | C/T | Ref/Ref | Ref/Ref |
| 14 | C/C | T/C | T/G | C/T | Var/Var | Hetero |
| 15 | C/C | T/T | T/G | C/T | Hetero | Var/Var |
| 16 | C/C | C/C | A/G | C/C | Var/Var | Hetero |
| 17 | C/A | T/C | G/G | C/C | Hetero | Var/Var |
| 18 | C/A | T/C | T/A | C/T | Hetero | Ref/Ref |
| 19 | C/C | T/C | A/G | C/C | Ref/Ref | Hetero |
| 20 | C/A | T/C | T/A | C/T | Ref/Ref | Ref/Ref |
| 21 | A/A | T/T | T/G | T/T | Ref/Ref | Hetero |
| 22 | A/A | T/C | T/G | C/T | Ref/Ref | Ref/Ref |
| 23 | C/A | T/C | A/G | C/C | Var/Var | Hetero |
| 24 | C/A | T/C | T/A | C/T | Hetero | Hetero |
| 25 | C/C | T/T | T/T | T/T | Hetero | Hetero |
| 26 | C/A | T/C | A/G | C/C | Var/Var | Ref/Ref |
| 27 | A/A | T/C | G/G | C/C | Ref/Ref | Hetero |
| 28 | C/A | C/C | A/G | C/C | Hetero | Hetero |
| 29 | C/C | C/C | A/G | C/C | Ref/Ref | Ref/Ref |
| 30 | C/C | T/T | G/G | C/C | Hetero | Ref/Ref |
| 31 | C/A | T/T | T/G | C/T | Ref/Ref | Var/Var |
| 32 | C/C | T/C | A/G | C/C | Hetero | Hetero |
| 33 | C/A | T/T | T/G | T/T | Hetero | Var/Var |
| 34 | C/A | T/T | T/G | T/T | Hetero | Var/Var |
| 35 | C/C | T/C | T/A | C/T | Hetero | Hetero |
| 36 | C/C | T/C | G/T | C/T | Ref/Ref | Var/Var |
| 37 | C/A | C/C | G/G | C/C | Hetero | Hetero |
| 38 | C/A | T/C | G/A | C/T | Hetero | Ref/Ref |
| 39 | C/C | T/C | T/A | C/C | Var/Var | Hetero |
| 40 | C/C | T/C | T/A | C/C | Ref/Ref | Ref/Ref |
| 41 | C/A | T/C | G/T | C/T | Ref/Ref | Ref/Ref |
| 42 | C/C | T/C | T/A | C/T | Ref/Ref | Ref/Ref |
| 43 | C/A | T/C | T/A | C/T | Ref/Ref | Hetero |
| 44 | C/C | T/T | T/T | T/T | Var/Var | Hetero |

Figure 4

| NO | Pretreatment | Dose | Standardized AUC | CLR | Standardized Cmax |
|---|---|---|---|---|---|
| 1 | 0 | 10 | 27.36 | 36.54971 | 4.337 |
| 2 | 0 | 10 | 15.277 | 65.45612 | 3.064 |
| 3 | 0 | 10 | 5.042 | 198.3504 | 0.58 |
| 4 | 1 | 4 | 23.27 | 42.97007 | 3.915 |
| 5 | 0 | 10 | 2.182 | 458.3539 | 0.253252015 |
| 6 | 1 | 6 | 1.915 | 522.3661 | 0.267831732 |
| 7 | 1 | 10 | 11.505 | 86.92095 | 1.231875043 |
| 8 | 0 | 8 | 18.625 | 53.67182 | 2.789534994 |
| 9 | 1 | 2 | 18.665 | 53.57371 | 3.884701284 |
| 10 | 1 | 8 | 5.861 | 170.5968 | 0.772064962 |
| 11 | 0 | 12 | 2.0867 | 479.3164 | 0.406739639 |
| 12 | 1 | 10 | 2.54 | 393.1771 | 0.4957823 |
| 13 | 0 | 10 | 18.718 | 53.42446 | 3.025055922 |
| 14 | 1 | 12 | 1.11 | 900.8777 | 0.280673924 |
| 15 | 0 | 12 | 13.106 | 76.30173 | 2.612301162 |
| 16 | 0 | 10 | 10.885 | 91.87008 | 1.30401363 |
| 17 | 0 | 8 | 14.73314391 | 67.87418 | 2.085374464 |
| 18 | 0 | 10 | 39.23206217 | 25.48936 | 5.58219203 |
| 19 | 1 | 2 | 13.97634328 | 71.54947 | 4.631147371 |
| 20 | 0 | 10 | 63.9338378 | 15.64117 | 7.601803551 |
| 21 | 0 | 10 | 39.50823094 | 25.31118 | 6.455895454 |
| 22 | 1 | 8 | 122.1283258 | 8.188109 | 17.52734211 |
| 23 | 1 | 6 | 26.15170328 | 38.23843 | 3.466019604 |
| 24 | 0 | 10 | 9.661881517 | 103.4995 | 1.402170798 |
| 25 | 0 | 10 | 3.04897251 | 327.9793 | 0.664167724 |
| 26 | 0 | 10 | 4.51704124 | 221.3839 | 0.538673945 |
| 27 | 1 | 10 | 14.39419844 | 69.47243 | 3.243792827 |
| 28 | 0 | 6 | 8.04560843 | 124.2914 | 0.961972427 |
| 29 | 0 | 10 | 45.95204227 | 21.76182 | 5.011694229 |
| 30 | 0 | 10 | 34.45711842 | 29.02158 | 5.418433477 |
| 31 | 1 | 6 | 19.67475183 | 50.82656 | 3.815778288 |
| 32 | 0 | 10 | 9.809162441 | 101.9455 | 2.402695362 |
| 33 | 0 | 10 | 14.01959253 | 71.32875 | 2.339097772 |
| 34 | 1 | 6 | 36.46605457 | 27.42276 | 5.503588273 |
| 35 | 0 | 10 | 11.18747621 | 89.38566 | 1.346425602 |
| 36 | 0 | 10 | 13.76877165 | 72.62812 | 2.314888679 |
| 37 | 0 | 6 | 13.19697229 | 75.77496 | 1.581569263 |
| 38 | 0 | 10 | 31.42477498 | 31.82203 | 3.551989556 |
| 39 | 0 | 10 | 17.00306276 | 58.81 | 2.154910099 |
| 40 | 0 | 10 | 36.79032136 | 27.18106 | 4.620629541 |
| 41 | 0 | 10 | 70.12233526 | 14.26079 | 14.13520766 |
| 42 | 0 | 10 | 56.51896048 | 17.69318 | 6.096472013 |
| 43 | 0 | 4 | 9.898585688 | 101.0245 | 1.32173503 |
| 44 | 1 | 10 | 16.50863919 | 60.57434 | 2.963002488 |

Figure 5

H: Hetero  V: Variant

Model A

| Intercept | UGT1A 1*6 211G>A H | UGT1A 1*6 211G>A V | UGT1A 7*2 387T>G H | UGT1A 7*2 387T>G V | UGT1A 9*1b -118T9>T10 H | UGT1A 9*1b -118T9>T10 V | BCRP 421C>A H | BCRP 421C>A V | ABC MDR1 1236T>C H | ABC MDR1 1236T>C V | ABC MDR1 2677G>T/A H | ABC MDR1 2677G>T/A V | ABC MDR1 3435C>T H | ABC MDR1 3435C>T V | NGS CPN2 Ref:G,Var:A H | NGS CPN2 Ref:G,Var:A V | NGS OR2B11 Ref:GA,Var:G H | NGS OR2B11 Ref:GA,Var:G V | Dose | Pretreatment |
|---|---|---|---|---|---|---|---|---|---|---|---|---|---|---|---|---|---|---|---|---|
| 4.471 | -0.367 | | -0.122 | | -0.041 | 0.021 | | 0.486 | -0.070 | | | 0.436 | -0.158 | 0.096 | -0.315 | -0.328 | -0.795 | -0.911 | -0.120 | -0.219 |

Model B

| Intercept | 1*6 H | 7*2 H | 9*1b H | 9*1b V | BCRP V | MDR1 1236 | MDR1 2677 H | MDR1 3435 H | MDR1 3435 V | CPN2 H | OR2B11 H | OR2B11 V | Dose |
|---|---|---|---|---|---|---|---|---|---|---|---|---|---|
| 4.311 | -0.410 | -0.196 | 0.107 | 0.310 | 0.916 | | 0.794 | -0.373 | 0.497 | -0.062 | -1.360 | -1.431 | -0.138 |

Model C

| Intercept | 7*2 V | 9*1b V | BCRP V | MDR1 2677 H | MDR1 3435 V | OR2B11 H | OR2B11 V | Dose |
|---|---|---|---|---|---|---|---|---|
| 4.132 | -0.191 | 0.364 | 1.081 | 0.686 | 0.677 | -1.379 | -1.547 | -0.141 |

Model D

| Intercept | 9*1b V | BCRP V | MDR1 2677 H | MDR1 3435 V | OR2B11 H | OR2B11 V | Dose |
|---|---|---|---|---|---|---|---|
| 4.067 | 0.508 | 1.124 | 0.705 | 0.683 | -1.410 | -1.577 | -0.150 |

Model E

| Intercept | 9*1b V | BCRP V | MDR1 3435 V | OR2B11 H | OR2B11 V | Dose |
|---|---|---|---|---|---|---|
| 4.462 | 0.493 | 1.161 | 0.400 | -1.497 | -1.563 | -0.129 |

Figure 6

H: Hetero  V: Variant

Model F

| Intercept | UGT1A 1*6 211G>A | | UGT1A 7*2 387T>G | | UGT1A 9*1b -118T9>T10 | | BCRP 421C>A | | ABC MDR1 1236T>C | | ABC MDR1 2677G>T/A | | ABC MDR1 3435C>T | | NGS CPN2 Ref:G, Var:A | | NGS OR2B11 Ref:GA, Var:G | | Dose | Pretreatment |
|---|---|---|---|---|---|---|---|---|---|---|---|---|---|---|---|---|---|---|---|---|
| | H | V | H | V | H | V | H | V | H | V | H | V | H | V | H | V | H | V | | |
| 4.456 | | | | | | 0.430 | | 1.213 | | | | | | | | | -1.365 | | -1.428 | -0.127 | |

Model G

| Intercept | UGT1A 1*6 211G>A | | UGT1A 7*2 387T>G | | UGT1A 9*1b -118T9>T10 | | BCRP 421C>A | | ABC MDR1 1236T>C | | ABC MDR1 2677G>T/A | | ABC MDR1 3435C>T | | NGS CPN2 Ref:G, Var:A | | NGS OR2B11 Ref:GA, Var:G | | Dose | Pretreatment |
|---|---|---|---|---|---|---|---|---|---|---|---|---|---|---|---|---|---|---|---|---|
| | H | V | H | V | H | V | H | V | H | V | H | V | H | V | H | V | H | V | | |
| 4.488 | | | | | | | | 1.171 | | | | | | | | | -1.285 | | -1.284 | -0.116 | |

Model H

| Intercept | UGT1A 1*6 211G>A | | UGT1A 7*2 387T>G | | UGT1A 9*1b -118T9>T10 | | BCRP 421C>A | | ABC MDR1 1236T>C | | ABC MDR1 2677G>T/A | | ABC MDR1 3435C>T | | NGS CPN2 Ref:G, Var:A | | NGS OR2B11 Ref:GA, Var:G | | Dose | Pretreatment |
|---|---|---|---|---|---|---|---|---|---|---|---|---|---|---|---|---|---|---|---|---|
| | H | V | H | V | H | V | H | V | H | V | H | V | H | V | H | V | H | V | | |
| 4.466 | | | | | | | | | | | | | | | | | -1.238 | | -1.367 | -0.105 | |

Model I

| Intercept | UGT1A 1*6 211G>A | | UGT1A 7*2 387T>G | | UGT1A 9*1b -118T9>T10 | | BCRP 421C>A | | ABC MDR1 1236T>C | | ABC MDR1 2677G>T/A | | ABC MDR1 3435C>T | | NGS CPN2 Ref:G, Var:A | | NGS OR2B11 Ref:GA, Var:G | | Dose | Pretreatment |
|---|---|---|---|---|---|---|---|---|---|---|---|---|---|---|---|---|---|---|---|---|
| | H | V | H | V | H | V | H | V | H | V | H | V | H | V | H | V | H | V | | |
| 3.060 | | | | | | | | 1.187 | | | | | | | | | | | | -0.057 | |

Model J

| Intercept | UGT1A 1*6 211G>A | | UGT1A 7*2 387T>G | | UGT1A 9*1b -118T9>T10 | | BCRP 421C>A | | ABC MDR1 1236T>C | | ABC MDR1 2677G>T/A | | ABC MDR1 3435C>T | | NGS CPN2 Ref:G, Var:A | | NGS OR2B11 Ref:GA, Var:G | | Dose | Pretreatment |
|---|---|---|---|---|---|---|---|---|---|---|---|---|---|---|---|---|---|---|---|---|
| | H | V | H | V | H | V | H | V | H | V | H | V | H | V | H | V | H | V | | |
| 4.758 | -0.571 | | | | | | | | | | | | | | | | -1.191 | | -1.312 | -0.126 | |

Figure 7

METHOD FOR DETERMINING PHARMACOKINETICS OF AXITINIB AND METHOD FOR PREDICTING THERAPEUTIC EFFECT OF AXITINIB BASED ON PHARMACOKINETICS OF AXITINIB

CROSS-REFERENCE TO RELATED APPLICATIONS

This application is a national stage application filed under 35 USC 371 of PCT/JP2018/019281, filed May 18, 2018, which claims the benefit of Japanese Patent Application No. 2017-100043, filed May 19, 2017, all of which is incorporated herein, in their entireties, by reference.

TECHNICAL FIELD

The present invention relates to a method for determining the pharmacokinetics of axitinib applicable to curatively unresectable or metastatic renal cell carcinoma or the like, and a method for predicting the therapeutic effect of axitinib based on the pharmacokinetics of axitinib.

BACKGROUND ART

Axitinib is an oral tyrosine kinase inhibitor that selectively inhibits vascular endothelial growth factor receptor (VEGFR)-1, -2, and -3. VEGFR-1, -2, and -3 are considered to participate in tumor growth and the infiltration (tumor spread) and metastasis of cancer. Axitinib is considered to exhibit antitumor activity by selectively inhibiting these VEGI-R-1, -2, and -3 and thereby suppressing angiogenesis and lymphangiogenesis and suppressing the growth and metastasis of tumor.

Axitinib is currently used as a molecular targeting drug for curatively unresectable or metastatic renal cell carcinoma. Although axitinib is a drug having a high therapeutic effect on such progressive renal cell carcinoma, it is difficult to predict its effect (rate of tumor reduction) or adverse reaction and to set the optimum dose. An oral dose of 10 mg/day is clinically a reference initial dose, but may vary within the dose range of 2 to 14 mg/day according to the presence or absence of adverse events such as diarrhea, dehydration, and blood pressure elevation. Tumor disappears completely in some clinical cases even while the dose is decreased. By contrast, for example, cases in which neither change in blood pressure nor a therapeutic effect is found even when the dose is increased as well as cases in which administration at the reference dose suddenly leads to brain hemorrhage have been reported.

It has been reported as to axitinib that its plasma concentration (pharmacokinetic analysis parameter; AUC: area under the curve) correlates with a therapeutic effect and adverse events (Non Patent Literature 1). Nonetheless, such a pharmacokinetic analysis parameter such as AUC is very difficult to measure in clinical settings due to the absence of a kit or a system for conveniently measuring the pharmacokinetic analysis parameter. If the measurement system was present, it would be very difficult for pragmatic clinical practice to carry out pharmacokinetic analysis, which requires blood collection at least 6 or 7 times, on every recipient patient.

In general, factors that define plasma drug concentrations can be broadly classified into three factors: [1] a dose, a dosing rate and the number of doses, [2] patient's body surface area, age and sex, and [3] a metabolic rate in the body. Among them, examples of the factor that defines the item [3] include the expression levels of metabolic enzymes. For example, it is known that the metabolic enzymes differ largely in expression level depending on genetic polymorphisms and consequently differ largely in metabolic rate. CYP3A4 and UGT1A have been reported as metabolic enzymes for axitinib (Non Patent Literature 2). Genetic polymorphisms in these metabolic enzymes have also previously been reported. For example, gene polymorphism UGT1A*28 is a polymorphism as to TATA box in a promoter region and results in seven (usually, six) TA repeat sequences, which in turn reduce the metabolic rates of drugs and increase toxicity ascribable to drug accumulation in the body, as demonstrated in drugs such as irinotecan.

However, the relation of gene polymorphisms in the aforementioned metabolic enzymes to plasma concentrations and toxicity is unknown about axitinib. Furthermore, there is no reason to apply the findings on irinotecan to axitinib.

Meanwhile, Patent Literature 1 discloses a method for evaluating the sensitivity of tumor to axitinib on the basis of a CD68 expression level in a tissue sample of the tumor. As for a molecular targeting drug erlotinib, which is an anticancer agent different from axitinib, a method for determining the degree of adverse reaction or efficacy of erlotinib on the basis of a polymorphism in human ABCB1 (*Homo sapiens* ATP-binding cassette, sub-family B (MDR/TAP), member 1) (P-glycoprotein) gene is known, as disclosed in, for example, Patent Literature 2. Specifically, Patent Literature 2 discloses that a predetermined genotype of the ABCB1 gene serves as an index for directly predicting the plasma concentration and toxicity of erlotinib.

However, the technique disclosed in Patent Literature 2 is a technique related to the epithelial growth factor receptor tyrosine kinase inhibitor erlotinib. Furthermore, the model does not directly predict the therapeutic effect of erlotinib, and complicated pharmacokinetic prediction was performed using only ABCB1 polymorphism. For these reasons, the technique cannot be applied to axitinib.

CITATION LIST

Patent Literature

Patent Literature 1: JP Patent Publication (Kokai) No. 2015-210268 A (2015)
Patent Literature 2: JP Patent Publication (Kokai) No. 2010-263810 A (2010)

Non Patent Literature

Non Patent Literature 1: Expert Opin. Drug Metab. Toxicol. (2012) 8 (2)
Non Patent Literature 2: J. Clin Pharmacol. (2013) 53: 491-504

SUMMARY OF INVENTION

Technical Problem

Accordingly, an object of the present invention is to provide methods for conveniently and highly accurately determining the pharmacokinetics of axitinib, and predicting the therapeutic effect of axitinib on the basis of the determined pharmacokinetics of axitinib, and determination apparatuses to which these methods are applied.

Solution to Problem

The present inventors have conducted diligent studies to attain the object and consequently completed the present invention by finding that: the pharmacokinetics of axitinib can be highly accurately predicted on the basis of a genotype related to a specific polymorphism of a test subject; and the therapeutic effect of axitinib can be highly accurately predicted on the basis of the predicted pharmacokinetics of axitinib. The present invention encompasses the following:

(1) A method for determining the pharmacokinetics of axitinib, comprising the steps of:
  acquiring information on the following items [1], [2] and [4] or the following items [1], [3] and [4]:
  [1] a polymorphism in OR2B11 gene,
  [2] a polymorphism in BCRP gene in which a mutant allele has a loss-of-function mutation,
  [3] a polymorphism in CPN2 gene, and
  [4] a dose of axitinib
regarding a test subject; and
  calculating a predicted pharmacokinetic parameter of axitinib on the basis of the items [1], [2] and [4] or the items [1], [3] and [4].

(2) The method for determining the pharmacokinetics of axitinib according to (1), wherein the item [1] is a polymorphism identified by rs35305980 in the OR2B11 gene or a polymorphism in linkage disequilibrium therewith.

(3) The method for determining the pharmacokinetics of axitinib according to (1), wherein the item [2] is C421A polymorphism identified by rs2231142 in the BCRP gene or a polymorphism in linkage disequilibrium therewith.

(4) The method for determining the pharmacokinetics of axitinib according to (1), wherein the item [3] is a polymorphism identified by rs4974539 in the CPN2 gene or a polymorphism in linkage disequilibrium therewith.

(5) The method for determining the pharmacokinetics of axitinib according to (1), further comprising:
  acquiring information on at least one item selected from the group consisting of the item [3] and the following items [5] to [9]:
  [5] a polymorphism in UGT1A1 gene in which a mutant allele has a loss-of-function mutation,
  [6] a polymorphism in UGT1A7 gene in which a mutant allele has a loss-of-function mutation,
  [7] a polymorphism in UGT1A9 gene in which a mutant allele has a gain-of-function mutation,
  [8] a polymorphism in MDR1 gene in which a mutant allele has a loss-of-function mutation, and
  [9] the presence or absence of pretreatment regarding the test subject, in addition to the items [1], [2] and [4]; and
  calculating the predicted pharmacokinetic parameter of axitinib on the basis of the items [1], [2] and [4] and the acquired information on at least one item selected from the group consisting of the items [3] and [5] to [9].

(6) The method for determining the pharmacokinetics of axitinib according to (5), wherein the item [5] is UGT1A1*6 polymorphism identified by rs4148323 in the UGT1 gene or a polymorphism in linkage disequilibrium therewith.

(7) The method for determining the pharmacokinetics of axitinib according to (5), wherein the item [6] is UGT1A7*2 polymorphism identified by rs17868323 in the UGT1 gene or a polymorphism in linkage disequilibrium therewith.

(8) The method for determining the pharmacokinetics of axitinib according to (5), wherein the item [7] is UGT1A9*1b polymorphism identified by rs3832043 in the UGT1 gene or a polymorphism in linkage disequilibrium therewith.

(9) The method for determining the pharmacokinetics of axitinib according to (5), wherein the item [8] is T1236C polymorphism identified by rs1128503, G2677T/A polymorphism identified by rs2032582 or C3435T polymorphism identified by rs1045642 in the MDR1 gene or a polymorphism in linkage disequilibrium therewith.

(10) The method for determining the pharmacokinetics of axitinib according to (5), wherein the item [3] is a polymorphism identified by rs4974539 in the CPN2 gene or a polymorphism in linkage disequilibrium therewith.

(11) The method for determining the pharmacokinetics of axitinib according to (1), wherein the predicted pharmacokinetic parameter is a predicted value of a standardized area under the plasma drug concentration-time curve (standardized AUC) (predicted standardized AUC value).

(12) The method for determining the pharmacokinetics of axitinib according to (11), wherein the predicted value of the standardized area under the plasma drug concentration-time curve (standardized AUC) (predicted standardized AUC value) is calculated according to a prediction expression in which the predicted standardized AUC value is decreased when there exists a mutant allele of the polymorphism of the item [1]; the predicted standardized AUC value is increased when there exists a mutant allele of the polymorphism of the item [2]; and the predicted standardized AUC value is decreased when there exists a mutant allele of the polymorphism of the item [3].

(13) The method for determining the pharmacokinetics of axitinib according to (5), wherein the predicted pharmacokinetic parameter is a predicted value of a standardized area under the plasma drug concentration-time curve (standardized AUC) (predicted standardized AUC value).

(14) The method for determining the pharmacokinetics of axitinib according to (13), wherein the predicted value of the standardized area under the plasma drug concentration-time curve (standardized AUC) (predicted standardized AUC value) is calculated according to a prediction expression in which the predicted standardized AUC value is decreased when there exists a mutant allele of the polymorphism of the item [5]; the predicted standardized AUC value is decreased when there exists a mutant allele of the polymorphism of the item [6]; and the predicted standardized AUC value is decreased when there exists a mutant allele of the polymorphism of the item [3].

(15) A method for predicting the therapeutic effect of axitinib, comprising the step of determining the antitumor activity and/or adverse reaction of axitinib on the basis of a predicted pharmacokinetic parameter of axitinib calculated by a method for determining the pharmacokinetics of axitinib according to any of (1) to (14).

(16) A determination apparatus for the pharmacokinetics of axitinib, comprising:
  an input part which inputs information on the following items [1], [2] and [4] or the following items [1], [3] and [4]:
  [1] a polymorphism in OR2B11 gene,
  [2] a polymorphism in BCRP gene in which a mutant allele has a loss-of-function mutation,
  [3] a polymorphism in CPN2 gene, and
  [4] a dose of axitinib
regarding a test subject; and
  an operation part which calculates a predicted pharmacokinetic parameter of axitinib on the basis of the items [1], [2] and [4] or the items [1], [3] and [4].

(17) The determination apparatus for the pharmacokinetics of axitinib according to (16), wherein the item [1] is a polymorphism identified by rs35305980 in the OR2B11 gene or a polymorphism in linkage disequilibrium therewith.

(18) The determination apparatus for the pharmacokinetics of axitinib according to (16), wherein the item [2] is C421A polymorphism identified by rs2231142 in the BCRP gene or a polymorphism in linkage disequilibrium therewith.
(19) The determination apparatus for the pharmacokinetics of axitinib according to (16), wherein the item [3] is a polymorphism identified by rs4974539 in the CPN2 gene or a polymorphism in linkage disequilibrium therewith.
(20) The determination apparatus for the pharmacokinetics of axitinib according to (16), wherein the input part further inputs information on at least one item selected from the group consisting of the item [3] and the following items [5] to [9]:
 [5] a polymorphism in UGT1A1 gene in which a mutant allele has a loss-of-function mutation,
 [6] a polymorphism in UGT1A7 gene in which a mutant allele has a loss-of-function mutation,
 [7] a polymorphism in UGT1A9 gene in which a mutant allele has a gain-of-function mutation,
 [8] a polymorphism in MDR1 gene in which a mutant allele has a loss-of-function mutation, and
 [9] the presence or absence of pretreatment
regarding the test subject, in addition to the items [1], [2] and [4], and
the operation part calculates the predicted pharmacokinetic parameter of axitinib on the basis of the items [1], [2] and [4] and the input information on at least one item selected from the group consisting of the items [3] and [5] to [9].
(21) The determination apparatus for the pharmacokinetics of axitinib according to (20), wherein the item [5] is UGT1A1*6 polymorphism identified by rs4148323 in the UGT1 gene or a polymorphism in linkage disequilibrium therewith.
(22) The determination apparatus for the pharmacokinetics of axitinib according to (20), wherein the item [6] is UGT1A7*2 polymorphism identified by rs17868323 in the UGT1 gene or a polymorphism in linkage disequilibrium therewith.
(23) The determination apparatus for the pharmacokinetics of axitinib according to (20), wherein the item [7] is UGT1A9*1b polymorphism identified by rs3832043 in the UGT1 gene or a polymorphism in linkage disequilibrium therewith.
(24) The determination apparatus for the pharmacokinetics of axitinib according to (20), wherein the item [8] is T1236C polymorphism identified by rs1128503, G2677T/A polymorphism identified by rs2032582 or C3435T polymorphism identified by rs1045642 in the MDR1 gene or a polymorphism in linkage disequilibrium therewith.
(25) The determination apparatus for the pharmacokinetics of axitinib according to (20), wherein the item [3] is a polymorphism identified by rs4974539 in the CPN2 gene or a polymorphism in linkage disequilibrium therewith.
(26) The determination apparatus for the pharmacokinetics of axitinib according to (16), wherein the predicted pharmacokinetic parameter is a predicted value of a standardized area under the plasma drug concentration-time curve (standardized AUC) (predicted standardized AUC value).
(27) The determination apparatus for the pharmacokinetics of axitinib according to (26), wherein the operation part calculates the predicted value of the standardized area under the plasma drug concentration-time curve (standardized AUC) (predicted standardized AUC value) according to a prediction expression in which the predicted standardized AUC value is decreased when there exists a mutant allele of the polymorphism of the item [1]; the predicted standardized AUC value is increased when there exists a mutant allele of the polymorphism of the item [2]; and the predicted standardized AUC value is decreased when there exists a mutant allele of the polymorphism of the item [3].
(28) The determination apparatus for the pharmacokinetics of axitinib according to (20), wherein the predicted pharmacokinetic parameter is a predicted value of a standardized area under the plasma drug concentration-time curve (standardized AUC) (predicted standardized AUC value).
(29) The determination apparatus for the pharmacokinetics of axitinib according to (28), wherein the operation part calculates the predicted value of the standardized area under the plasma drug concentration-time curve (standardized AUC) (predicted standardized AUC value) according to a prediction expression in which the predicted standardized AUC value is decreased when there exists a mutant allele of the polymorphism of the item [5]; the predicted standardized AUC value is decreased when there exists a mutant allele of the polymorphism of the item [6]; and the predicted standardized AUC value is decreased when there exists a mutant allele of the polymorphism of the item [3].
(30) A prediction apparatus for the therapeutic effect of axitinib, comprising an operation part which determines the antitumor activity and/or adverse reaction of axitinib on the basis of a predicted pharmacokinetic parameter of axitinib calculated with a determination apparatus for the pharmacokinetics of axitinib according to any of (16) to (29).

The present specification encompasses the contents disclosed in Japanese Patent Application No. 2017-100043 on which the priority of the present application is based.

Advantageous Effects of Invention

The method and the apparatus for determining the pharmacokinetics of axitinib according to the present invention can highly accurately predict a pharmacokinetic parameter of axitinib by a very convenient method.

The method and the apparatus for determining the therapeutic effect of axitinib according to the present invention can highly accurately predict the antitumor effect and/or adverse reaction of axitinib on the basis of the predicted pharmacokinetic parameter of axitinib.

Thus, the present invention can provide supporting information effective for determining an appropriate dose of axitinib to a patient in need of axitinib.

BRIEF DESCRIPTION OF DRAWINGS

[FIG. 3-1] FIG. 3 is a diagram showing a list of genotype analysis results of predetermined gene polymorphisms as to 44 cases used in Examples.

[FIG. 3-2] FIG. 3 is a diagram showing a list of genotype analysis results of predetermined gene polymorphisms as to 44 cases used in Examples.

[FIG. 3-3] FIG. 3 is a diagram showing a list of genotype analysis results of predetermined gene polymorphisms as to 44 cases used in Examples.

FIG. 4 is a diagram showing a list of results of analyzing background factors, rates of tumor reduction, the presence or absence of adverse reaction, and pharmacokinetic parameters of patients as to 44 cases used in Examples.

FIG. 5 is a diagram showing the configuration of a prediction expression constructed using information on gene polymorphisms, and background factors and actually measured AUC values of patients, and a coefficient of the prediction expression as to 44 cases used in Examples.

FIG. 6 is a diagram showing the configuration of a prediction expression constructed using information on gene polymorphisms, and background factors and actually measured AUC values of patients, and a coefficient of the prediction expression as to 44 cases used in Examples.

FIG. 7 is a diagram showing the configuration of a prediction expression constructed using information on gene polymorphisms, and background factors and actually measured AUC values of patients, and a coefficient of the prediction expression as to 44 cases used in Examples.

DESCRIPTION OF EMBODIMENTS

Figure 1:
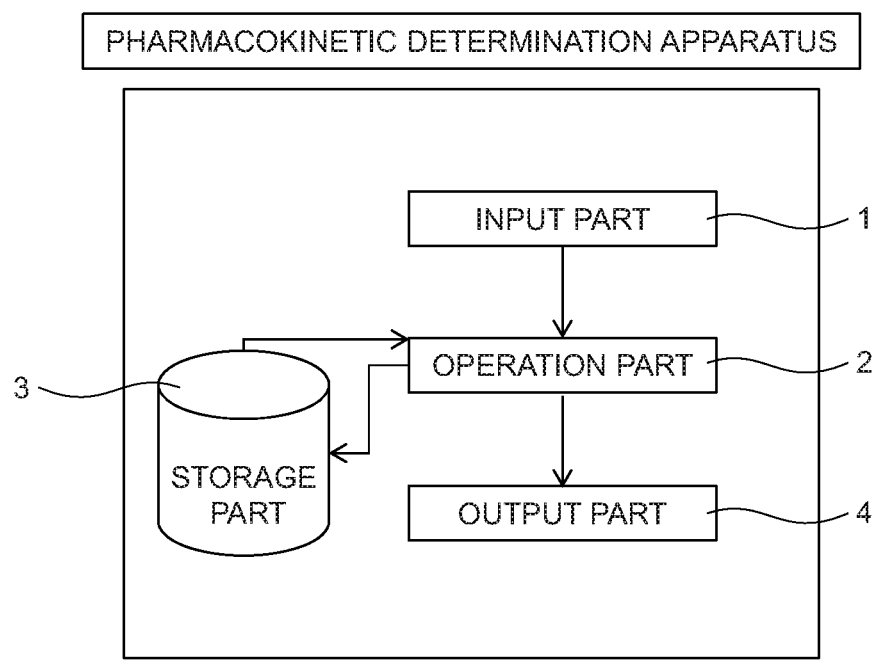
FIG. 1 is a block diagram schematically showing a determination apparatus for the pharmacokinetics of axitinib to which the present invention is applied.

Hereinafter, the present invention will be described in detail.

SUMMARY

In the present invention, the pharmacokinetics of axitinib is predicted on the basis of predetermined background factors in a recipient patient for axitinib, and predetermined gene polymorphisms in the patient. Specifically, a pharmacokinetic parameter related to axitinib is calculated as a predicted value (predicted pharmacokinetic parameter). The calculated predicted pharmacokinetic parameter can be utilized in the determination of the therapeutic effect of axitinib. An appropriate dose of axitinib for each patient can be determined by determining the therapeutic effect of axitinib on the basis of the predicted pharmacokinetic parameter.

The background factors and the gene polymorphisms can each be acquired as information for each patient by interview and genotype analysis. Alternatively, the background factors may be acquired on the basis of past medical records or the like. Therefore, interview is not necessarily required for predicting the pharmacokinetics of axitinib by the application of the present invention. Also, the gene polymorphisms can be acquired by various analysis methods using a biological sample (blood, cells, etc.) collected from a patient. Alternatively, for the gene polymorphisms, results of genotype analysis conducted for another examination or treatment may be utilized, or data read out of a database, if any, in which individual genotype data is stored may be utilized. Thus, the collection of a biological sample and genotype analysis are not necessarily required for predicting the pharmacokinetics of axitinib by the application of the present invention as to the gene polymorphisms.

The predetermined background factors and the predetermined gene polymorphisms in the patient can both be regarded as explanatory variables (dependent variables) when the predicted pharmacokinetic parameter is used as an objective variable. In other words, the predicted pharmacokinetic parameter which is an objective variable can be calculated according to a prediction expression with the predetermined background factors and the predetermined gene polymorphisms in the patient as explanatory variables.

In this context, axitinib is a substituted indazole derivative and is a tyrosine kinase inhibitor (TM) that inhibits vascular endothelial growth factor receptor VEGFR-1, -2 and -3. The molecular formula of axitinib is $C_{22}H_{18}N_4OS$. Its molecular weight is 386.47, and its chemical name is N-methyl-2-({3-[(1E)-2-(pyridin-2-yl)ethen-1-yl]-1H-indazol-6-yl}sulfanyl) benzamide. Axitinib is known to be mainly metabolized by CYP3A4/5 and partially metabolized by CYP1A2, CYP2C19 and UGT1A1 in the liver. Axitinib is sold under a trade name of Inlyta with efficacy and effect on curatively unresectable or metastatic renal cell carcinoma.

In this context, the pharmacokinetics of axitinib means disposition related to, particularly, the metabolism and excretion of axitinib. Thus, examples of the parameter indicating the pharmacokinetics of axitinib can include, but are not particularly limited to, parameters related to the metabolism and excretion of axitinib, for example, total clearance (CLtot), an area under the plasma drug concentration-time curve (AUC) and elimination half-life.

The total clearance is defined as a volume-based value of the amount of a drug metabolized and excreted per time. Specifically, the total clearance is a value of [volume]/[time] as a unit and is indicated by, for example, a unit (mL/min). The total clearance can be calculated by determining an elimination rate from the amount of a drug eliminated by metabolism in the liver and excretion in the kidney, and dividing the elimination rate by the plasma concentration of the drug.

The area under the plasma drug concentration-time curve is a value obtained by integrating a plasma concentration with time as to a graph of the plasma concentration on the ordinate against the time on the abscissa (plasma drug concentration-time curve). Specifically, the area under the plasma drug concentration-time curve is a value indicating the total amount of a drug utilized in the body. The standardized area under the plasma drug concentration-time curve is a value obtained by statistically standardizing (dividing by a dose (mg/day) of a drug) a measured value of the area under the plasma drug concentration-time curve. The aforementioned total clearance (CLtot) is a value obtained by dividing the dose of a drug by the area under the plasma drug concentration-time curve (AUC).

The half-life means time required for a drug to decrease at a primary elimination rate from a predetermined concentration to half the concentration.

[Background Factor and Gene Polymorphism]

The predetermined background factors in a patient and the predetermined gene polymorphisms in the patient for use in predicting the pharmacokinetics of axitinib will be described in detail.

The predetermined background factors in a patient for use in predicting the pharmacokinetics of axitinib are meant to include information on a dose of axitinib and the presence or absence of pretreatment in the patient. For the dose of axitinib, the dose itself may be used as an explanatory variable, or the dose may be divided into predetermined ranges, and a predetermined value can be assigned as an explanatory variable to each of the ranges. In order to set explanatory variables of the predetermined ranges of the divided dose, higher numerical values can be used as explanatory variables with increase in dose, depending on how to establish the prediction expression.

For the information on the presence or absence of pretreatment, for example, explanatory variables can be set to 0 for a patient without pretreatment and 1 for a patient with pretreatment, depending on how to establish the prediction expression. In this context, the pretreatment is meant to include chemotherapy and immunotherapy of cancer. Examples of the chemotherapy include the administration of molecular targeting drugs, except for axitinib, such as sorafenib, sunitinib, everolimus, temsirolimus and pazopanib. Examples of the immunotherapy include the administration of interferon (INF) and interleukin-2.

The gene polymorphisms in the patient for use in predicting the pharmacokinetics of axitinib are gene polymorphisms defined in the following items [1] to [3]:

[1] a polymorphism in OR2B11 gene,

[2] a polymorphism in BCRP gene in which a mutant allele has a loss-of-function mutation, and

[3] a polymorphism in CPN2 gene.

Examples of the polymorphism defined in the item [1] can include a polymorphism identified by rs35305980 in the OR2B11 gene and a polymorphism in linkage disequilibrium therewith. The polymorphism identified by rs35305980 is a polymorphism of wild-type guanine-alanine (GA) to guanine (G) in a mutant. The OR2B11 gene is known as a gene encoding olfactory receptor family-2, subfamily-B, member-11.

Examples of the polymorphism defined in the item [2] can include C421A polymorphism identified by rs2231142 in the BCRP gene and a polymorphism in linkage disequilibrium therewith. The C421A polymorphism, a polymorphism in the BCRP gene, is a gene polymorphism of cytosine at position 421 of a coding region to adenine. This single-nucleotide variation mutates glutamine at position 141 in the BCRP protein to lysine and markedly reduces a transport function of capturing and ejecting a substrate drug (loss-of-function mutation).

Examples of the polymorphism defined in the item [3] can include a polymorphism identified by rs4974539 in the CPN2 gene and a polymorphism in linkage disequilibrium therewith. The polymorphism identified by rs4974539 is a polymorphism of wild-type guanine to adenine in a mutant. The CPN2 gene is known as a gene encoding polypeptide 2 of carboxypeptidase N.

In addition to the gene polymorphisms defined in the items [1] to [3], one or more of gene polymorphisms defined in the following items [5] to [8]:

[5] a polymorphism in UGT1A1 gene in which a mutant allele has a loss-of-function mutation,

[6] a polymorphism in UGT1A7 gene in which a mutant allele has a loss-of-function mutation,

[7] a polymorphism in UGT1A9 gene in which a mutant allele has a gain-of-function mutation, and

[8] a polymorphism in MDR1 gene in which a mutant allele has a loss-of-function mutation may be used as the gene polymorphisms in the patient for use in predicting the pharmacokinetics of axitinib.

Examples of the polymorphism defined in the item [5] can include UGT1A1*6 polymorphism identified by rs4148323 and a polymorphism in linkage disequilibrium therewith. UGT1A1*6, a polymorphism in the UGT1A1 gene, is a gene polymorphism of guanine (G) at position 211 included in exon 1 in a majority of wild-type alleles (UGT1A1*1) to adenine (A). This single-nucleotide variation mutates glycine at amino acid position 71 in the UGT1A1 protein to arginine so that mutant UGT1A1 enzyme has lower enzymatic activity than that of wild-type (loss-of-function mutation).

Examples of the polymorphism defined in the item [6] can include UGT1A7*2 polymorphism identified by rs17868323 and a polymorphism in linkage disequilibrium therewith. UGT1A7*2, a polymorphism in the UGT1A7 gene, is a gene polymorphism of thymine at position 387 of a coding region in a majority of wild-type alleles to guanine in a mutant. This mutant UGT1A7 enzyme has lower enzymatic activity than that of wild-type (loss-of-function mutation).

Examples of the polymorphism defined in the item [7] can include UGT1A9*1b polymorphism identified by rs3832043 and a polymorphism in linkage disequilibrium therewith. UGT1A9*1b, a polymorphism in the UGT1A9 gene, is a gene polymorphism of wild-type 9 sequences of (dT) ((dT)$_9$) starting at position −118 of a promoter region to 10 sequences of d(T) ((dT)$_{10}$). This single-nucleotide variation, i.e., the insertion of thymine, elevates the expression level of the gene and consequently elevates UGT activity (gain-of-function mutation).

Examples of the polymorphism defined in the item [8] can include T1236C polymorphism identified by rs1128503, G2677T/A polymorphism identified by rs2032582, and C3435T polymorphism identified by rs1045642 in the MDR1 gene and a polymorphism in linkage disequilibrium with any of these polymorphisms. The T1236C polymorphism, a polymorphism in the MDR1 gene, is a gene polymorphism of cytosine at position 1236 of a coding region to thymine. This single-nucleotide variation does not involve amino acid substitution in the MDR1 protein, but influences the stability of mRNA and reduces an mRNA level in a genotype having a minor allele T (loss-of-function mutation). The G2677T/A polymorphism identified by rs2032582 is a gene polymorphism of guanine at position 2677 of the coding region to thymine or adenine. This single-nucleotide variation is also a loss-of-function mutation. The C3435T polymorphism identified by rs1045642 is a gene polymorphism of cytosine at position 3435 of the coding region to thymine. This single-nucleotide variation is also a loss-of-function mutation.

Meanwhile, the polymorphism in linkage disequilibrium defined in the items [1] to [3] and [5] to [8] is not particularly limited and can be a polymorphism in linkage disequilibrium with linkage disequilibrium coefficient D' of 0.8 or more, more preferably 0.95 or more, further preferably 0.99 or more, most preferably 1. The linkage disequilibrium means that alleles at two loci are liked to each other and inherited with frequency larger than that of the case where the alleles at the loci are each independently inherited. When alleles of a first gene polymorphism of two gene polymorphisms is defined as (A,a); alleles of a second gene polymorphism are defined as (B,b); and the frequencies of four haplotype (AB, Ab, aB, and ab) are defined as PAB, PAb, PaB, and Pab, respectively, the linkage disequilibrium coefficient D' is obtained according to the following expression:

$$D'=(PABPab-PAbPaB)/\text{Min}[(PAB+PaB)(PaB+Pab), (PAB+PAb)(PAb+Pab)]$$

wherein Min[(PAB+PaB)(PaB+Pab),(PAB+PAb)(PAb+Pab)] represents that a smaller value of (PAB+PaB)(PaB+Pab) and (PAB+PAb)(PAb+Pab) is adopted.

For the presence or absence of the gene polymorphisms defined in the items [1] to [3] and [5] to [8], explanatory variables can be set to 0 for homozygous wild-type alleles, 1 for the gene polymorphism that is heterozygous, and 2 for the gene polymorphism that is homozygous, depending on how to establish the prediction expression. However, the explanatory variables set as to the gene polymorphisms defined in the items [1] to [3] and [5] to [8] are not limited by this specific example and may be set at nonequal intervals such as 0, 1 and 3 in the order described above. Alternatively, one polymorphism may be defined by 2 variables, which can be set to (0,0) for homozygous wild-type alleles, (1,0) for the gene polymorphism that is heterozygous, and (0,1) for the gene polymorphism that is homozygous.

[Prediction Expression]

As mentioned above, a predicted pharmacokinetic parameter for each patient is calculated according to the prediction expression in which the predetermined background factors in the patient and the predetermined gene polymorphisms in the patient are used as explanatory variables, and the pharmacokinetic parameter of axitinib is used as an objective variable. The prediction expression is not limited by any means and can be obtained by regression analysis using the background factors and the gene polymorphisms in an actual patient, and an actually measured standardized AUC value. In the regression analysis, for example, nonlinear multiple regression analysis approaches such as power models, exponential models, asymptotic exponential models, logistic growth models and Gompertz growth models can be used without particular limitations. These approaches can be used in combination with linear multiple regression models such as ridge regression models, lasso regression models, and elastic net.

The prediction expression thus obtained is shown as one example in Examples. A predicted standardized AUC value can be calculated from the predetermined background factors in a patient and the predetermined gene polymorphisms in the patient as mentioned above. In this case, the prediction expression includes each independent term as to the gene polymorphisms of the items [1] and [2] or the items [1] and [3] and a term as to the dose of axitinib, and a coefficient related to each term is set.

The prediction expression may be an expression including each independent term as to one or more gene polymorphisms selected from the group consisting of the item [3] and the items [5] to [8] and a term as to the dose of axitinib, in addition to the terms of the gene polymorphisms of the items [1] and [2].

For example, the prediction expression for predicting the standardized AUC value can be a prediction expression in which the predicted standardized AUC value is decreased when there exists a mutant allele of the polymorphism of the item [1]; the predicted standardized AUC value is increased when there exists a mutant allele of the polymorphism of the item [2]; the predicted standardized AUC value is decreased when there exists a mutant allele of the polymorphism of the item [3]; the predicted standardized AUC value is decreased when there exists a mutant allele of the polymorphism of the item [5]; and the predicted standardized AUC value is decreased when there exists a mutant allele of the polymorphism of the item [6].

The prediction expression is preferably an expression that has the largest influence on the predicted standardized AUC value to be calculated when there exists a mutant allele of the polymorphism of the item [1] among the gene polymorphisms of the items [1] to [3] and [5] to [8], and has the second largest influence on the predicted standardized AUC value to be calculated when there exists a mutant allele of the polymorphism of the item [2]. In this context, the influence on the predicted standardized AUC value to be calculated can be adjusted by the magnitude of the absolute value of the coefficient. For example, the absolute value of the coefficient related to the term as to the polymorphism of the item [1] can be rendered larger than that of the coefficient related to the term as to the polymorphism of the item [2] so that the influence of the case where there exists a mutant allele of the polymorphism of the item [1] on the predicted standardized AUC value to be calculated is relatively larger than that of the case where there exists a mutant allele of the polymorphism of the item [2].

The prediction expression for predicting the pharmacokinetic parameter may be set to include a term as to the presence or absence of pretreatment, terms as to other gene polymorphisms, or terms as to other background factors, in addition to the terms as to the items [1] to [3] and [5] to [8] and the term as to the dose of axitinib. Examples of other gene polymorphisms can include polymorphisms in other genes included in the UGT1A1 gene, the UGT1A7 gene or the UGT1A9 gene. Examples of other background factors can include patient's age, sex, histopathological diagnosis results, and preexisting conditions.

A confidence interval can be further estimated for the predicted pharmacokinetic parameter such as the predicted standardized AUC value to be calculated according to the prediction expression. The confidence interval may be an interquartile range or may be a 95% confidence interval by assuming a normal distribution. If the predicted pharmacokinetic parameter calculated according to the prediction expression falls outside the confidence interval, this can be assessed to be unpredictable.

[Determination of Therapeutic Effect of Axitinib]

As mentioned above, the pharmacokinetic parameter of axitinib for a patient can be predicted on the basis of the predetermined background factors in the patient and the predetermined gene polymorphisms in the patient. The therapeutic effect of axitinib on the patient can be determined on the basis of the predicted pharmacokinetic parameter.

In this context, the therapeutic effect of axitinib is meant to include both an effect of ameliorating cancer to be treated and adverse reaction ascribable to the administration of axitinib. Specifically, the emergence of the cancer-ameliorating effect and adverse reaction brought about by the administration of axitinib to the patient can be assessed with high accuracy on the basis of the predicted pharmacokinetic parameter.

Examples of the cancer to be treated with axitinib can include renal cell carcinoma, particularly, curatively unresectable or metastatic renal cell carcinoma. However, the present invention is not limited by these examples. Examples of the cancer to be treated with axitinib include: sarcoma such as fibrosarcoma, malignant fibrous histiocytoma, liposarcoma, rhabdomyosarcoma, leiomyosarcoma, angiosarcoma, Kaposi's sarcoma, lymphangiosarcoma, synovial sarcoma, chondrosarcoma, and osteosarcoma; carcinoma such as brain tumor, head and neck cancer, breast cancer, lung cancer, esophageal cancer, stomach cancer, duodenal cancer, appendix cancer, colon cancer, rectal cancer, liver cancer, pancreatic cancer, gallbladder cancer, bile duct cancer, anus cancer, ureter cancer, bladder cancer, prostate cancer, penis cancer, testis cancer, uterus cancer, ovary cancer, vulva cancer, vagina cancer, and skin cancer; and leukemia and malignant lymphoma.

Thus, the effect of axitinib on these cancers can be predicted for the patient on the basis of the predicted pharmacokinetic parameter of axitinib. The effect of ameliorating cancer by axitinib is not particularly limited and can be evaluated from, for example, a rate of tumor reduction. The rate of tumor reduction can be calculated in accordance with Response evaluation criteria in solid tumors (RECIST version 1.1) by "calculating the baseline sum of the diameters of target lesions (longest diameters for lesions other than malignant lymph nodes and short axes for the malignant lymph nodes) as baseline sum diameters (a), subtracting from the post-treatment sum of the diameters of target lesions, dividing the resulting value (b) by the baseline sum diameters, and multiplying the resulting value (a) by 100", i.e., according to the expression: 100×[(a)−(b)]/(a). In addition, the effect of ameliorating cancer by axitinib may be assessed on the basis of the size, the number and the development site, etc. of tumor in MRI images or CT images.

Examples of the adverse reaction ascribable to the administration of axitinib can include proteinuria. However, the present invention is not limited by these examples. Examples of the adverse reaction of axitinib can include diarrhea, hypertension, fatigue, nausea, decreased appetite, dysphonia, hand-and-foot syndrome, hypothyroidism, asthenia, vomiting, weight loss, mucosal inflammation, stomatitis, eruption, constipation, headache, dry skin, dysgeusia, increased TSH levels, nausea, increased AST (GOT) levels, increased ALT (GPT) levels, epistaxis, arthralgia, increased ALP levels, bellyache, increased LDH levels, malaise, coughing, chest pain, reduced blood platelet counts and edema. Examples of the serious adverse reaction ascribable to the administration of axitinib can include hypertension, high blood pressure crisis, arterial thromboembolism, venous thromboembolism, bleeding, perforation of the digestive tract and fistula formation, disturbed thyroid functions, protracted wound healing, posterior reversible encephalopathy syndrome, hepatic dysfunction and heart failure.

Thus, the presence or absence and the degree of emergence of the adverse reaction ascribable to axitinib can be predicted for the patient on the basis of the predicted pharmacokinetic parameter of axitinib.

As mentioned above, the therapeutic effect of axitinib can be determined for each patient on the basis of the predicted pharmacokinetic parameter. Therapeutic strategy with axitinib can be optimized for each patient by using the determination results. The therapeutic strategy with axitinib is meant to include the dose and timing of administration of axitinib. Particularly, the dose of axitinib is preferably optimized for each patient by using the determination results.

Specifically, when the metabolism and excretion of axitinib are assessed as being slow from the predicted pharmacokinetic parameter (e.g., when the predicted standardized AUC value is a high value), the emergence of adverse reaction can be predicted. Therefore, the dose of axitinib can be decreased. On the other hand, when the metabolism and excretion of axitinib are assessed as being fast from the predicted pharmacokinetic parameter (e.g., when the predicted standardized AUC value is a low value), the low likelihood of adverse reaction and low antitumor activity can be predicted. Therefore, the dose of axitinib can be increased. Provided that the predicted pharmacokinetic parameter is at or around a median value (e.g., in the range of 25 to 50 percentiles), a usual dose of axitinib can be used.

The usual dose of axitinib is 5 mg per dosage which is orally administered twice a day (10 mg/day) to an adult. Thus, when the dose of axitinib is decreased in the aforementioned case, the dose is set to an amount of less than 10 mg/day, for example, 7 mg/day. When the dose of axitinib is increased in the aforementioned case, the dose is set to an amount of larger than 10 mg/day, for example, 14 mg/day.

[Pharmacokinetic Determination Apparatus and Therapeutic Effect Determination Apparatus]

The determination apparatus for the pharmacokinetics of axitinib according to the present invention is an apparatus for predicting a pharmacokinetic parameter of axitinib as to a patient on the basis of predetermined background factors in the patient and predetermined gene polymorphisms in the patient as mentioned above.

The pharmacokinetic determination apparatus comprises, as shown in, for example, FIG. 1, input part 1 which inputs information on predetermined background factors in a patient and predetermined gene polymorphisms in the patient, and operation part 2 which calculates a predicted pharmacokinetic parameter of axitinib on the basis of the information input by the input part 1. Also, the pharmacokinetic determination apparatus may comprise storage part 3 which stores the information input by the input part 1 or the predicted pharmacokinetic parameter calculated by the operation part 2. Furthermore, the pharmacokinetic determination apparatus may comprise output part 4 which outputs the predicted pharmacokinetic parameter calculated by the operation part 2 or the predicted pharmacokinetic parameter stored in the storage part 3.

The pharmacokinetic determination apparatus can be realized by a so-called computer. Specifically, the input part 1 in the pharmacokinetic determination apparatus means an input device such as a keyboard or a mouse for the computer, or an input interface with an external storage device (public database, etc.). The operation part 2 means CPU or the like having an operational function of calculating the predicted pharmacokinetic parameter according to the aforementioned prediction expression on the basis of the input information. The storage part 3 can be an internal memory or hard disk drive of the computer, or an external storage device. The storage part 3 can be shared by a plurality of pharmacokinetic determination apparatuses.

In the pharmacokinetic determination apparatus thus configured, the input part 1 inputs predetermined background factors in a patient and predetermined gene polymorphisms in the patient. Information on these items may be input by a user or may be input from, for example, a gene polymorphism analysis apparatus. In the latter case, the pharmacokinetic determination apparatus is connected to a genotype analysis apparatus, and information on genotypes output from the genotype analysis apparatus is input thereto. The input information on the background factors and/or the gene polymorphisms may be stored in the storage part 3 by the operation part 2.

The operation part 2 calculates a predicted pharmacokinetic parameter using the information on the background factors and/or the gene polymorphisms input by the input part 1 or stored in the storage part 3, and the prediction expression for calculating the predicted pharmacokinetic parameter. In this context, the prediction expression may be stored in the storage part 3 or may be input from the input part 1. The predicted pharmacokinetic parameter calculated by the operation part 2 can be output to the output part 4, for example, a display or a printer. The predicted pharmacokinetic parameter calculated by the operation part 2 may be output to another computer or a device such as a tablet via a network such as internet or intranet, though these components are not shown in FIG. 1.

The operation part 2 assesses whether the calculated predicted pharmacokinetic parameter falls within or outside the preset confidence interval described above, and can output "unpredictable" when the predicted pharmacokinetic parameter falls outside the confidence interval.

Meanwhile, the determination apparatus for the therapeutic effect of axitinib according to the present invention is an apparatus for determining the therapeutic effect of axitinib on the basis of a pharmacokinetic parameter predicted by predicting the pharmacokinetic parameter of axitinib for a patient on the basis of predetermined background factors in the patient and predetermined gene polymorphisms in the patient as mentioned above.

Figure 2:
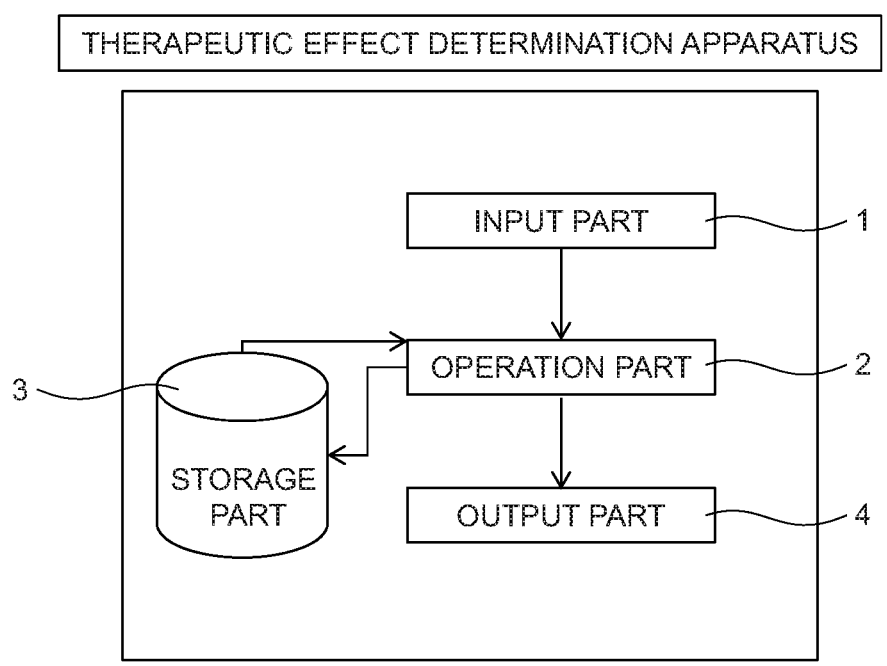
FIG. 2 is a block diagram schematically showing a determination apparatus for the therapeutic effect of axitinib to which the present invention is applied.

The therapeutic effect determination apparatus comprises, as shown in, for example, FIG. 2, input part 1 which inputs information on predetermined background factors in a patient and predetermined gene polymorphisms in the patient, and operation part 2 which calculates a predicted pharmacokinetic parameter of axitinib on the basis of the information input by the input part 1, and determines the therapeutic effect of axitinib on the basis of the predicted pharmacokinetic parameter. Also, the therapeutic effect determination apparatus may comprise storage part 3 which stores the information input by the input part 1 or the predicted pharmacokinetic parameter and/or the therapeutic effect calculated by the operation part 2. Furthermore, the therapeutic effect determination apparatus may comprise output part 4 which outputs the predicted pharmacokinetic parameter and/or the therapeutic effect calculated by the operation part 2 or the predicted pharmacokinetic parameter and/or the therapeutic effect stored in the storage part 3.

In the therapeutic effect determination apparatus shown in FIG. 2, the same reference numerals will be used to designate the same or similar configurations as those in the pharmacokinetic determination apparatus shown in FIG. 1, so that the description will be omitted. Particularly, in the therapeutic effect determination apparatus shown in FIG. 2, the operation part 3 determines the predicted rate of tumor reduction and/or likelihood of emergence of adverse reaction as the therapeutic effect of axitinib on the basis of the predicted pharmacokinetic parameter. Also, the therapeutic effect determination apparatus may draw therapeutic strategy (dose and/or timing of administration) with axitinib on the basis of the predicted therapeutic effect.

EXAMPLES

Hereinafter, the present invention will be described in more detail with reference to Examples. However, the technical scope of the present invention is not limited by Examples given below.

Example 1

In this Example, models for predicting an area under the plasma drug concentration-time curve (AUC; one of the pharmacokinetic analysis parameters) confirmed to correlate with the therapeutic effect or adverse reaction of axitinib were prepared using regression models with related gene polymorphism information and patient background factors as variables.
<Experimental Method>
(1) Administration of Axitinib
a) Study Patient The study patients were progressive renal cell carcinoma patients who were diagnosed with renal cell carcinoma at 20 years of age or older at the Department of Urology, Yamaguchi University Hospital, would plan to receive treatment with axitinib, and voluntarily agreed to join this study by understanding the contents of "informed consent documents" and signing a "letter of consent".
b) Axitinib Administration Method
1) Axitinib was orally administered at a standard initial dose of 10 mg (5 mg per dosage).
2) When hypertension reportedly serving as a clinical parameter for dose increase did not appear, the dose was increased to 14 mg (7 mg per dosage).

3) When an adverse event of grade 2 (based on adverse event evaluation criteria of NCI CTCAE ver. 4.0) appeared, the administration was resumed at a dose of 10 mg after drug holidays. When an adverse event of grade 3 appeared, the administration was resumed at a dose decreased to 7 mg after drug holidays.
(2) Gene Polymorphism Analysis DNA was extracted (approximately 1 μL) from mononuclear cell components in the peripheral blood (10 ml) of each patient and dispensed to two containers. The DNA in one of the containers was hybridized to template DNA on GeneChip (kindly provided by Toyo Kohan Co., Ltd.) base chip, and fluorescence intensity was quantified with a dedicated reader to determine genotypes of UGT1A1*6, UGT1A1*28, UGT1A1*60, UGT1A7*12, UGT1A7*2, UGT1A9*1b, UGT1A1*93, UGT1A4*1b, UGT1A4*3, UGT1A5*3, UGT1A5*6, BCRP (421C>A), MDR1 (1236T>C), MDR1 (2677G>T/A) and MDR1 (3435C>T). The results of analyzing the genotypes are shown in FIGS. 3-1 to 3-3. Further, gene polymorphisms in exon regions were comprehensively analyzed by exome sequencing with Illumina NextSeq 500 to calculate gene polymorphisms related to amino acid substitution having large influence on pharmacokinetic analysis results. Technical validation was conducted by Sanger sequencing. Then, gene polymorphisms exhibiting significant correlation with the plasma concentration of axitinib were calculated at several locations. From among them, a gene polymorphism in CPN2 gene and a gene polymorphism in OR2B11 gene exhibiting positive correlation with the plasma concentration were determined.
(3) Pharmacokinetic Concentration Analysis Pharmacokinetic concentration analysis was conducted on patients who gave the consent and were scheduled to receive axitinib, each time the drug dose was changed. Blood collection was performed 8 days or later after the start of drug administration (8 days or later after the restart of drug administration if the administration was discontinued, i.e., after administration for 7 consecutive days). After securing of a blood collection route to an indwelling catheter for the vein, blood collection (5 ml) was performed before administration of axitinib and 1, 2, 3, 4, 8, and 12 hours after the administration, and plasma axitinib concentrations were measured. The blood collection route was rendered usable plural times by heparin injection (0.5 ml) after blood collection, and 2 ml of blood was discarded before blood collection, followed by blood collection for samples. The measurement was performed by liquid chromatography (LC MS/MS), and the maximum serum concentration (Cmax), the time to the maximum serum concentration (Tmax), an area under the serum concentration curve (AUC), and apparent serum elimination half-life (T1/2) were calculated by the extended least squares method to determine extensive metabolizers and slow metabolizers.
(4) Construction of Regression Models Of the measurement results described above in the paragraph (3), the respective numerical values of standardized AUC, CLR and standardized Cmax, the presence or absence of pretreatment, and the dose were summarized in FIG. 4. Regression models (exponential regression models) for estimating standardized AUC on the basis of 13 gene polymorphisms and 2 factors involving six gene polymorphisms related to UGT1A, one gene polymorphism related to CYP3A, four gene polymorphisms related to ABC-related gene, two new gene polymorphisms (gene polymorphism in CPN2 gene and gene polymorphism in OR2B11 gene) identified in the paragraph (2) as well as the presence or absence of pretreatment and the dose were constructed using the results shown in FIGS. 3-1 to 3-3 and 4. The regression models used were exponential function models represented by the following expression:

$$y=\exp\{\Sigma b_i x_i + b_0\} \quad \text{[Expression 1]}$$

Here, in this Example, 13×2+2=28 variables were used in which one genotype was indicated by two variables of (xi and xi+1); (0,0), (1,0) and (0,1) were assigned to wild-type, heterozygous and mutant alleles, respectively; and the 13 gene polymorphisms, the presence or absence of pretreatment and the dose were each defined as xi. The standardized AUC value was defined as y. $b_0$ to $b_{28}$ were determined as to the 44 cases shown in FIGS. 3-1 to 3-3 and 4 such that the square error of y from the predicted value (right-hand side) in the expression described above was minimized <Analysis Results>

First, all 28 variables were narrowed down as candidates to 15 variables consisting of 9 gene polymorphisms (13 variables) and the presence or absence of pretreatment, and the dose using lasso regression models. Next, from among the 15 variables, the factors (gene polymorphisms, the dose, and the presence or absence of pretreatment) were decreased by backward selection such that the coefficient of determination was maximized, to search for combinations with a fewer number of variables and high correlation between a standardized AUC value and a predicted standardized AUC value. In this context, it is also possible to search for the optimum combination by using the backward selection for all 28 variables from the start. In this case, variables once excluded cannot be used. Therefore, better combinations may be obtained by some search methods in combination. For example, SFS or SFFS for use in statistical pattern recognition may be used for the combinatorial optimization. Alternatively, all combinations may be evaluated by all-possible selection to determine the optimum combination. The combination with high correlation may be selected as a combination of variables having the largest coefficient of correlation or a combination of variables highly relevant on a prepared scatter diagram of standardized AUC values and predicted standardized AUC values.

In this Example, an exponential function model having a coefficient of correlation of 0.82 between the standardized AUC value and the predicted standardized AUC value [model G] was constructed by the method described above using 4 variables (two gene polymorphisms and doses): C421A polymorphism (rs2231142) in the BCRP gene, a polymorphism (rs35305980) in the OR2B11 gene, and the doses.

Figure 7:
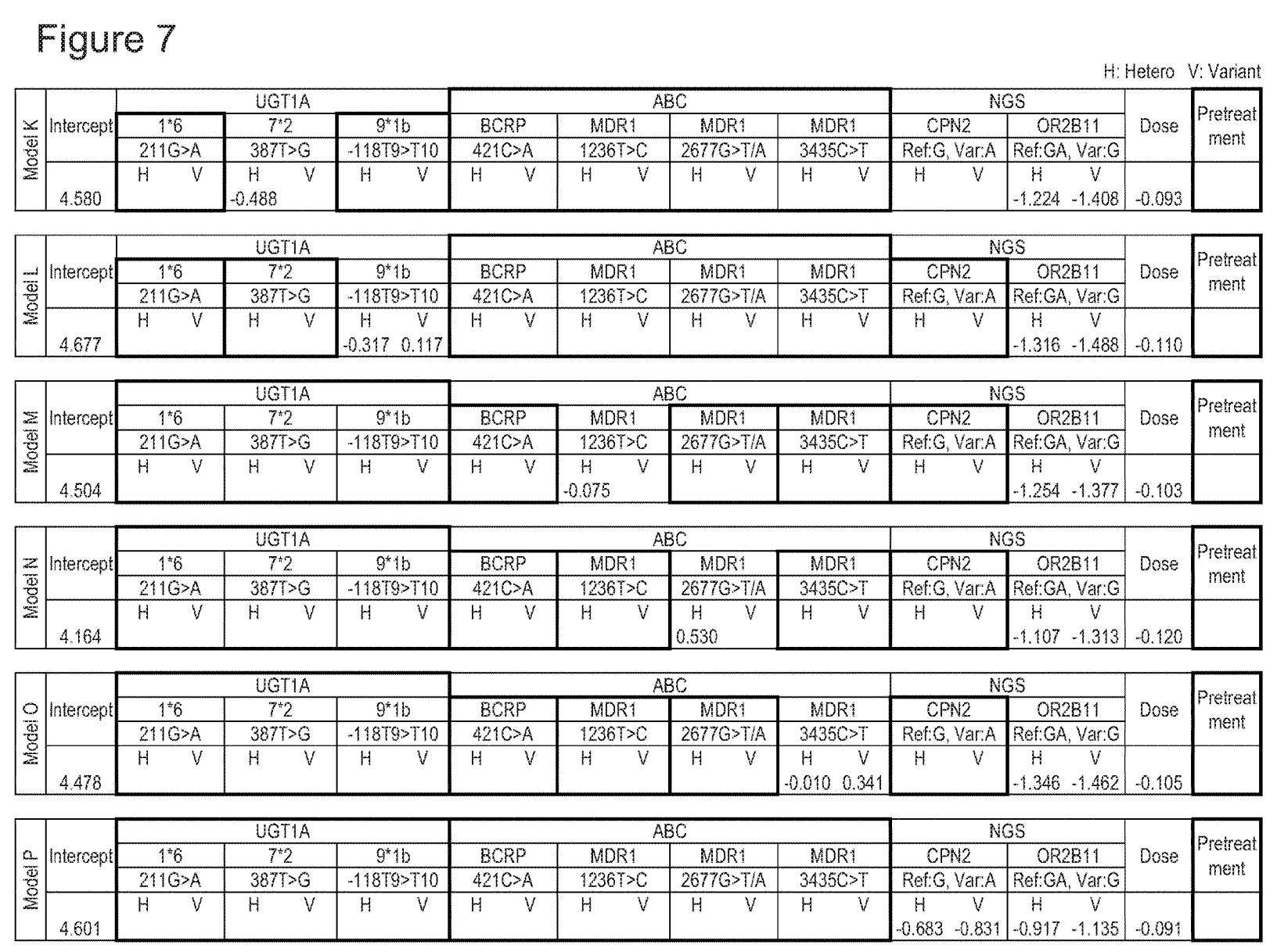

Models A to P were constructed by increase or decrease in variables with the model G as a reference. The factors (gene polymorphisms, the dose and the presence or absence of pretreatment) included in the models A to P and calculated coefficients were summarized in FIGS. 5 to 7. In FIGS. 5 to 7, the box with a thin line depicts a factor included in each model, and the box with a thick line depicts a factor that was not included in each model. In FIGS. 5 to 7, a numerical value described under each factor means a coefficient in the expression described above, and the expression is defined by the coefficient to form a prediction expression for calculating standardized AUC values. Thus, the absolute value of the coefficient related to each factor represents the strength of influence on the prediction of predicted standardized AUC values. A positive coefficient means that the predicted standardized AUC value is increased with increase in numerical value. A negative coefficient means that the predicted standardized AUC is decreased with decrease in numerical value. A coefficient closer to 0 (smaller absolute value) means smaller influence on the prediction. "Intercept" in FIGS. 5 to 7 means intercept $b_0$ in the prediction expression.

Tables 1 to 3 show the coefficients of correlation (For model construction) between standardized AUC values and predicted standardized AUC values in model construction using 44 cases as to models A to P, the coefficients of correlation (For model construction) between standardized AUC values and predicted standardized AUC values of 7 cases in the application of the constructed models to 7 cases for validation, and the coefficients of correlation (Total data) between standardized AUC values and predicted standardized AUC values of 51 cases consisting of the 44 cases for model construction and the 7 cases for validation.

TABLE 1

|  |  | Coefficient of correlation |
|---|---|---|
| Model A | For model construction | 0.832907632 |
|  | Data for validation | 0.827114282 |
|  | Total data | 0.765173207 |
|  | The number of polymorphisms | 9 |
| Model B | For model construction | 0.889239624 |
|  | Data for validation | 0.896493751 |
|  | Total data | 0.752627672 |
|  | The number of polymorphisms | 8 |
| Model C | For model construction | 0.885503652 |
|  | Data for validation | 0.946717549 |
|  | Total data | 0.784172451 |
|  | The number of polymorphisms | 6 |
| Model D | For model construction | 0.877753808 |
|  | Data for validation | 0.92706526 |
|  | Total data | 0.773619584 |
|  | The number of polymorphisms | 5 |
| Model E | For model construction | 0.852162429 |
|  | Data for validation | 0.938880472 |
|  | Total data | 0.762761626 |
|  | The number of polymorphisms | 4 |

TABLE 2

|  |  | Coefficient of correlation |
|---|---|---|
| Model F | For model construction | 0.838056803 |
|  | Data for validation | 0.968669128 |
|  | Total data | 0.724673242 |
|  | The number of polymorphisms | 3 |
| Model G | For model construction | 0.817698798 |
|  | Data for validation | 0.946146872 |
|  | Total data | 0.702923367 |
|  | The number of polymorphisms | 2 |
| Model H | For model construction | 0.623511678 |
|  | Data for validation | 0.928363401 |
|  | Total data | 0.588161509 |
|  | The number of polymorphisms | 1 |
| Model I | For model construction | 0.455180781 |
|  | Data for validation | 0.555878768 |
|  | Total data | 0.377277688 |
|  | The number of polymorphisms | 1 |
| Model J | For model construction | 0.65080002 |
|  | Data for validation | 0.885523324 |
|  | Total data | 0.576260183 |
|  | The number of polymorphisms | 2 |

TABLE 3

|  |  | Coefficient of correlation |
|---|---|---|
| Model K | For model construction | 0.737619631 |
|  | Data for validation | 0.874327284 |
|  | Total data | 0.69785632 |
|  | The number of polymorphisms | 2 |

TABLE 3-continued

| | | Coefficient of correlation |
|---|---|---|
| Model L | For model construction | 0.617221793 |
| | Data for validation | 0.95385904 |
| | Total data | 0.615861391 |
| | The number of polymorphisms | 2 |
| Model M | For model construction | 0.607912012 |
| | Data for validation | 0.90615249 |
| | Total data | 0.57769134 |
| | The number of polymorphisms | 2 |
| Model N | For model construction | 0.674921382 |
| | Data for validation | 0.895970703 |
| | Total data | 0.606732291 |
| | The number of polymorphisms | 2 |
| Model O | For model construction | 0.630017182 |
| | Data for validation | 0.810133055 |
| | Total data | 0.620134411 |
| | The number of polymorphisms | 2 |
| Model P | For model construction | 0.715894779 |
| | Data for validation | 0.963240353 |
| | Total data | 0.716244024 |
| | The number of polymorphisms | 2 |

As shown in FIGS. 5 to 7 and Tables 1 to 3, a 3-variable model [model H] which excluded the C421A polymorphism in the BCRP gene from the model G had a coefficient of correlation of 0.623 between the standardized AUC value and the predicted standardized AUC value. A 2-variable model [model I] which excluded the gene polymorphism (rs35305980) in the OR2B11 gene from the model G had a coefficient of correlation of 0.46 between the standardized AUC value and the predicted standardized AUC value. As is thus evident from the comparison of the coefficient of correlation of the model G with the coefficient of correlation of the model H or the model I, the latter coefficient of correlation was markedly decreased. Accordingly, the C421A polymorphism in the BCRP gene and the gene polymorphism (rs35305980) in the OR2B11 gene were found by this Example to be factors essential for the prediction models.

As shown in Tables 1 to 3, when the model G was applied to 7 cases for validation, the coefficient of correlation between the standardized AUC values and the predicted standardized AUC values of the 7 cases was 0.95, and the coefficient of correlation from 51 cases consisting of 44 cases for model construction and the 7 cases for validation was 0.70, showing high correlation.

As shown in FIGS. 5 to 7 and Tables 1 to 3, models A to F prepared by further adding a factor to the model G exhibited a higher coefficient of correlation than that of the model G. This demonstrated that a prediction expression having better accuracy can be constructed by further adding a factor to the model G. Specifically, it was demonstrated that one or more gene polymorphisms selected from among UGT1A1*6 polymorphism identified by rs4148323, UGT1A7*2 polymorphism identified by rs17868323, UGT1A9*1b polymorphism identified by rs3832043, T1236C polymorphism identified by rs1128503 in the MDR1 gene, G2677T/A polymorphism identified by rs2032582 in the MDR1 gene, C3435T polymorphism identified by rs1045642 in the MDR1 gene and a gene polymorphism identified by rs4974539 in the CPN2 gene can be included as factors to construct a prediction expression having better accuracy.

As one example, the model C was a prediction model based on 6 gene polymorphisms (the UGT1A7*2 polymorphism identified by rs17868323, the UGT1A9*1b polymorphism identified by rs3832043, the G2677T/A polymorphism identified by rs2032582 in the MDR1 gene, and the C3435T polymorphism identified by rs1045642 in the MDR1 gene plus the gene polymorphisms of the model G) and the dose. Specifically, the model C was constructed as a model that appeared when the number of factors was set to 8 by backward selection from the variables obtained by narrowing down using the aforementioned Lasso regression model. The model C had a coefficient of correlation of 0.88 between the standardized AUC values of 44 cases and the predicted standardized AUC value of this prediction model, which exhibited higher correlation that that of the coefficient of correlation of model G. Further, the model C had a coefficient of correlation of 0.95 between the standardized AUC values of 7 cases for validation and the predicted standardized AUC value of this prediction model, and a coefficient of correlation of 0.78 between the standardized AUC values of 51 cases consisting of the 44 cases for model construction and the 7 cases for validation and the predicted standardized AUC value.

Figure 8:
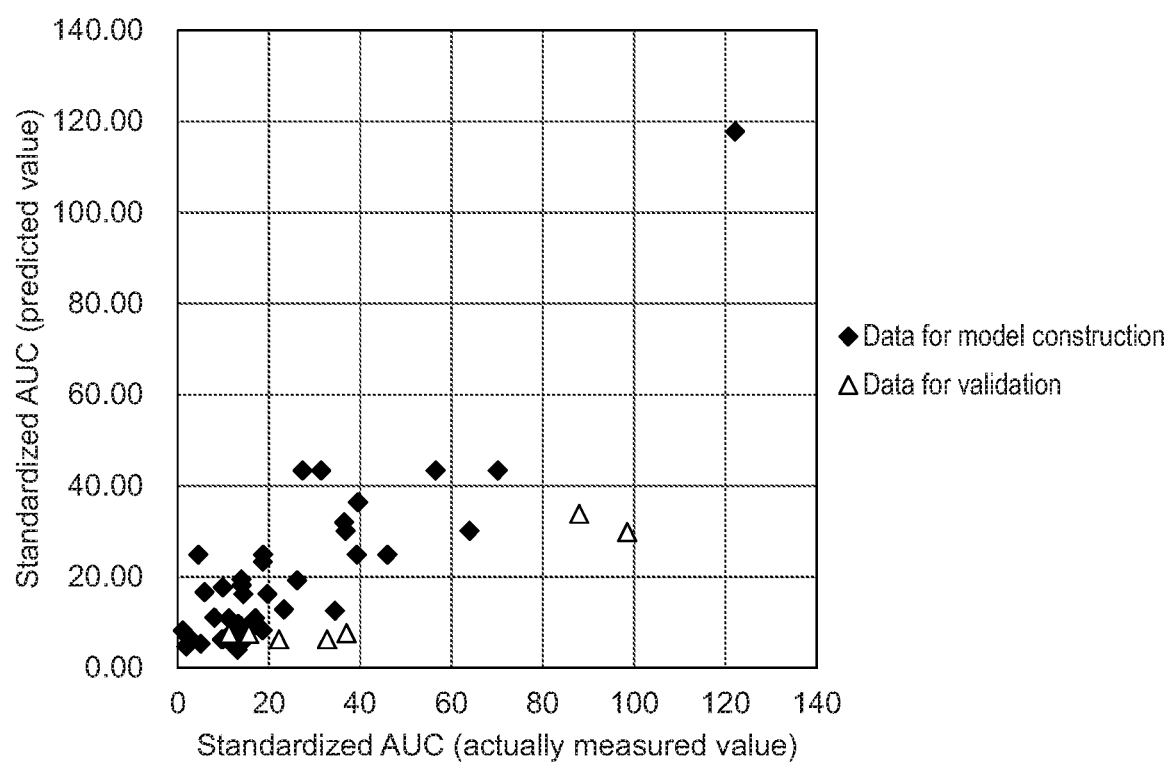
FIG. 8 is a characteristic diagram showing results of comparing a predicted standardized AUC value calculated using a prediction expression of model C identified in Example 1 with an actually measured AUC value.

As one example, results of comparing the predicted standardized AUC value calculated using the model C with an actually measured standardized AUC value are shown in FIG. 8. It can also be understood from FIG. 8 that the predicted standardized AUC value calculated using these 8 factors correlates highly with the actually measured standardized AUC value.

On the other hand, the model P was a prediction model that differed from the model G in that the model P did not include the C421A polymorphism in the BCRP gene and employed the gene polymorphism identified by rs4974539 in the CPN2 gene as a factor. Specifically, the model P was a prediction model based on the factors: the gene polymorphism identified by rs35305980 in the OR2B11 gene, the gene polymorphism identified by rs4974539 in the CPN2 gene, and the dose. The model P had a coefficient of correlation of 0.72 between the standardized AUC values of 44 cases and the predicted standardized AUC value of this prediction model and was thus found to be able to ensure sufficient prediction accuracy, though its coefficient of correlation was lower than that of the model G. Correlation was increased. Further, the model P had a coefficient of correlation of 0.96 between the standardized AUC values of 7 cases for validation and the predicted standardized AUC value of this prediction model, and a coefficient of correlation of 0.72 between the standardized AUC values of 51 cases consisting of the 44 cases for model construction and the 7 cases for validation and the predicted standardized AUC value. These results demonstrated that an excellently accurate prediction expression can be constructed in which the gene polymorphism identified by rs35305980 in the OR2B11 gene, the gene polymorphism identified by rs4974539 in the CPN2 gene, and the dose are used as factors.

All publications, patents and patent applications cited herein are incorporated herein by reference in their entirety.

We claim:

1. A method for determining the pharmacokinetics of axitinib, comprising the steps of:
   acquiring information on the following items [1], [2] and [4] or the following items [1], [3] and [4]:
   [1] a polymorphism in OR2B11 gene,
   [2] a polymorphism in BCRP gene in which a mutant allele has a loss-of-function mutation,
   [3] a polymorphism in CPN2 gene, and
   [4] a dose of axitinib regarding a test subject; and
   calculating a predicted pharmacokinetic parameter of axitinib on the basis of the items [1], [2] and [4] or the items [1], [3] and [4].

2. The method for determining the pharmacokinetics of axitinib according to claim 1, wherein the item [1] is a polymorphism identified by rs35305980 in the OR2B11 gene or a polymorphism in linkage disequilibrium therewith.

3. The method for determining the pharmacokinetics of axitinib according to claim 1, wherein the item [2] is C421A polymorphism identified by rs2231142 in the BCRP gene or a polymorphism in linkage disequilibrium therewith.

4. The method for determining the pharmacokinetics of axitinib according to claim 1, wherein the item [3] is a polymorphism identified by rs4974539 in the CPN2 gene or a polymorphism in linkage disequilibrium therewith.

5. The method for determining the pharmacokinetics of axitinib according to claim 1, further comprising:
  acquiring information on at least one item selected from the group consisting of the item [3] and the following items [5] to [9]:
    [5] a polymorphism in UGT1A1 gene in which a mutant allele has a loss-of-function mutation,
    [6] a polymorphism in UGT1A7 gene in which a mutant allele has a loss-of-function mutation,
    [7] a polymorphism in UGT1A9 gene in which a mutant allele has a gain-of-function mutation,
    [8] a polymorphism in MDR1 gene in which a mutant allele has a loss-of-function mutation, and
    [9] the presence or absence of pretreatment regarding the test subject, in addition to the items [1], [2] and [4]; and
  calculating the predicted pharmacokinetic parameter of axitinib on the basis of the items [1], [2] and [4] and the acquired information on at least one item selected from the group consisting of the items [3] and [5] to [9].

6. The method for determining the pharmacokinetics of axitinib according to claim 5, wherein the item [5] is UGT1A1*6 polymorphism identified by rs4148323 in the UGT1 gene or a polymorphism in linkage disequilibrium therewith, the item [6] is UGT1A7*2 polymorphism identified by rs17868323 in the UGT1 gene or a polymorphism in linkage disequilibrium therewith, the item [7] is UGT1A9*1b polymorphism identified by rs3832043 in the UGT1 gene or a polymorphism in linkage disequilibrium therewith, the item [8] is T1236C polymorphism identified by rs1128503, G2677T/A polymorphism identified by rs2032582 or C3435T polymorphism identified by rs1045642 in the MDR1 gene or a polymorphism in linkage disequilibrium therewith, and the item [3] is a polymorphism identified by rs4974539 in the CPN2 gene or a polymorphism in linkage disequilibrium therewith.

7. The method for determining the pharmacokinetics of axitinib according to claim 1, wherein the predicted pharmacokinetic parameter is a predicted value of a standardized area under the plasma drug concentration-time curve (standardized AUC) (predicted standardized AUC value).

8. The method for determining the pharmacokinetics of axitinib according to claim 7, wherein the predicted value of the standardized area under the plasma drug concentration-time curve (standardized AUC) (predicted standardized AUC value) is calculated according to a prediction expression in which the predicted standardized AUC value is decreased when there exists a mutant allele of the polymorphism of the item [1]; the predicted standardized AUC value is increased when there exists a mutant allele of the polymorphism of the item [2]; and the predicted standardized AUC value is decreased when there exists a mutant allele of the polymorphism of the item [3].

9. The method for determining the pharmacokinetics of axitinib according to claim 5, wherein the predicted pharmacokinetic parameter is a predicted value of a standardized area under the plasma drug concentration-time curve (standardized AUC) (predicted standardized AUC value).

10. The method for determining the pharmacokinetics of axitinib according to claim 9, wherein the predicted value of the standardized area under the plasma drug concentration-time curve (standardized AUC) (predicted standardized AUC value) is calculated according to a prediction expression in which the predicted standardized AUC value is decreased when there exists a mutant allele of the polymorphism of the item [5]; the predicted standardized AUC value is decreased when there exists a mutant allele of the polymorphism of the item [6]; and the predicted standardized AUC value is decreased when there exists a mutant allele of the polymorphism of the item [3].

11. A method for predicting the therapeutic effect of axitinib, comprising the step of determining the antitumor activity and/or adverse reaction of axitinib on the basis of a predicted pharmacokinetic parameter of axitinib calculated by a method for determining the pharmacokinetics of axitinib according to claim 1.

12. A method for predicting the therapeutic effect of axitinib, comprising the step of determining the antitumor activity and/or adverse reaction of axitinib on the basis of a predicted pharmacokinetic parameter of axitinib calculated by a method for determining the pharmacokinetics of axitinib according to claim 5.

13. The method of claim 1, comprising the further step of administering axitinib to the test subject to treat a cancer.

* * * * *